United States Patent
Schneider et al.

(10) Patent No.: US 10,736,611 B2
(45) Date of Patent: Aug. 11, 2020

(54) ULTRASOUND IMAGING OF FAST-MOVING STRUCTURES

(71) Applicant: KONINKLIJKE PHILIPS N.V., Eindhoven (NL)

(72) Inventors: Robert Joseph Schneider, Eindhoven (NL); David Prater, Eindhoven (NL); William Robert Martin, Eindhoven (NL); Scott William Dianis, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 1217 days.

(21) Appl. No.: 14/771,231

(22) PCT Filed: Jan. 31, 2014

(86) PCT No.: PCT/IB2014/058694
§ 371 (c)(1),
(2) Date: Aug. 28, 2015

(87) PCT Pub. No.: WO2014/135996
PCT Pub. Date: Sep. 12, 2014

(65) Prior Publication Data
US 2016/0015367 A1    Jan. 21, 2016

Related U.S. Application Data

(60) Provisional application No. 61/771,979, filed on Mar. 4, 2013.

(51) Int. Cl.
*A61B 8/00* (2006.01)
*A61B 8/08* (2006.01)
(Continued)

(52) U.S. Cl.
CPC .......... *A61B 8/543* (2013.01); *A61B 8/0883* (2013.01); *A61B 8/13* (2013.01); *A61B 8/463* (2013.01);
(Continued)

(58) Field of Classification Search
CPC ....... A61B 8/543; A61B 8/5207; A61B 8/463; A61B 8/13; A61B 8/0883; A61B 8/5284; A61B 8/483; G01S 7/52087
See application file for complete search history.

(56) References Cited

U.S. PATENT DOCUMENTS 5,099,847 A * 3/1992 Powers ............... A61B 5/0456
600/443
5,709,210 A * 1/1998 Green .................. A61B 5/0456
600/453
(Continued)

FOREIGN PATENT DOCUMENTS

JP        54135476 A      10/1979
JP          06186 A       1/1994
(Continued)

OTHER PUBLICATIONS

Devore et al "Spatio-Temporal Image Correlation.." Ultrasound Obstet. Gynocol. vol. 22, (2003) p. 380-387.
(Continued)

*Primary Examiner* — Amanda Lauritzen Moher (57) ABSTRACT

An ultrasonic diagnostic imaging system is gated to acquire images at different phases of a physiological cycle such as the heartbeat. At each successive heart cycle a trigger actuates the acquisition of a continuous sequence of images, starting at a particular phase of the heart cycle and ending when the next heart cycle begins. Multiple triggers are used, each starting at a different phase of the heart cycle and each acquiring images at uniform temporal spacing. After the first trigger is used a sequence of images has been captured
(Continued)

which are temporally evenly spaced over the heart cycle, and as successive triggers are used uniform temporal spacing is maintained as the heart cycle is filled in with additional images for replay of an image loop of phase re-ordered images at a high frame rate of display.

16 Claims, 4 Drawing Sheets

(51) Int. Cl.
    *A61B 8/13*     (2006.01)
    *G01S 7/52*     (2006.01)

(52) U.S. Cl.
    CPC .......... *A61B 8/5207* (2013.01); *A61B 8/5284* (2013.01); *A61B 8/483* (2013.01); *G01S 7/52087* (2013.01)

(56) References Cited

U.S. PATENT DOCUMENTS

| | | | |
|---|---|---|---|
| 5,993,390 A | 11/1999 | Savord | |
| 5,997,479 A | 12/1999 | Savord | |
| 6,210,333 B1 | 4/2001 | Gardner | |
| 6,436,048 B1 | 8/2002 | Pesque | |
| 2003/0092991 A1 | 5/2003 | Sehgal | |
| 2005/0143777 A1* | 6/2005 | Sra | G16H 50/50 607/4 |
| 2005/0203393 A1* | 9/2005 | Brekke | A61B 8/08 600/437 |
| 2006/0241383 A1 | 10/2006 | Camus | |
| 2007/0038103 A1* | 2/2007 | Kobayashi | A61B 8/14 600/443 |
| 2008/0240355 A1* | 10/2008 | Ohishi | A61B 6/4441 378/98 |
| 2009/0156937 A1 | 6/2009 | Sasaki | |

FOREIGN PATENT DOCUMENTS

| | | |
|---|---|---|
| JP | 0678926 A | 3/1994 |
| JP | 2001224591 A | 8/2001 |
| JP | 2001252271 | 9/2001 |
| WO | 2011004475 A1 | 1/2011 |

OTHER PUBLICATIONS

Brekke et al, "Tissue Doppler Gated (TDOG) Dynamic Three-Dimensional Ultrasound.." Ultrasound Obsted. Gynocol. 2004 24 p. 192-198.

Karadayi et al, "Automatic Image-Based Gating for 4d Ultrasound" Proceedings of the 28th IEEE, EMBS Annual International Conference, Aug 30-Sep. 3, 2006 p. 2388-2391.

* cited by examiner

ULTRASOUND IMAGING OF FAST-MOVING STRUCTURES

This application is the U.S. National Phase application under 35 U.S.C. § 371 of International Application No. PCT/IB2014/058694, filed on Jan. 31, 2014, which claims the benefit of U.S. Application No. 61/771,979 filed on Mar. 4, 2013. These applications are hereby incorporated by reference herein.

This invention relates to medical diagnostic ultrasound systems and, in particular, to ultrasound systems used to image rapidly and periodically moving structures such as a beating heart.

One of the important uses for diagnostic ultrasound imaging is diagnosing the performance of the heart. This is due to the fact that ultrasound can view the heart beating in real time with non-ionizing radiation. While ultrasound imaging is relatively fast in image frame acquisition and is able to provide real-time (or "live") imaging of fast moving structures, gating methods are often employed to achieve even faster image (or frame) rates to better visualize fast moving structures. Gating is the act of acquiring images relative to some external physiological event which often occurs periodically over time. For ultrasound, this event is typically related to either the respiration or cardiac cycle in adult, pediatric, and/or fetal studies. The event is monitored typically through an external sensor, such as the ECG signal used for monitoring relative time in the cardiac cycle, but can also be monitored from the image content. With gated acquisition, heart images can be acquired over several periodic heart cycles and at varying times or phases in the heart cycle. After the image frames have been acquired they are re-ordered according to their relative times of acquisition (phases) in the periodic cycle instead of their absolute time (i.e. relative to their original sequence of acquisition.) The re-ordered image frames can then be played back at a higher image rate than can be realized over a single heart cycle, and at a higher frame rate of display than otherwise could be achieved in the original acquisition. An example of this acquisition and reordering is shown in FIG. 1 of U.S. Pat. No. 5,099,847 (Powers et al.) This patent shown a first sequence of images acquired at odd-numbered heart phases, followed by acquisition of a second sequence of images at even-numbered heart phases. FIG. 2 of the patent shows the re-ordering of the images by heart phase, forming a sequence of twice as many images during a heart cycle. This sequence can be "looped", that is played from beginning to end the immediately replayed from the beginning, giving the appearance of a heart beating while displayed in a high frame rate display sequence. A similar approach can be used to form live, three dimensional images of the beating heart as described in U.S. Pat. No. 5,993,390 (Savord et al.)

There are two approaches to performing gating. The approach described above in the Powers et al. and Savord et al. patents is called active, or prospective, gating in which image data is acquired at pre-specified times in the cardiac cycle. In the Powers et al. patent, for instance, acquisition is pre-specified to be at odd-numbered phases initially, followed by acquisition at even-numbered phases. The advantage of this approach is that images are acquired adequately and evenly over the periodic cycle. However, a typical drawback of this approach is that the re-ordered frame rate has to be pre-specified so as to specify exactly when images should be acquired relative to the gating event, the ECG signal, and the duration of the heart cycle will vary from patient to patient and even from time to time for the same patient. Another drawback is that this method can take a long time to acquire all of the necessary data, as substantial delays may need to be inserted into the acquisition to ensure that all of the desired times in the periodic cycle are sampled.

Another gating approach is called retrospective gating. In this approach, images are acquired continuously (i.e., when the acquisition of one image is completed, another one starts immediately) over many successive physiological cycles in what is typically called a real-time or "live" mode, irrespective of the relative time in the periodic cycle. However, the time of acquisition of each image relative to the external event is monitored throughout the acquisition so that the images can be re-ordered later once acquisition has been completed. A variation of this technique called "STIC" (spatio-temporal image correlation) is commonly used to assemble high frame rate image sequences of the fetal heart. See, e.g., "Spatio-temporal image correlation (STIC): new technology for evaluation of the fetal heart," G. R. Devore et al., *Ultrasound Obstet. Gynecol.*, vol. 22 (2003) at pp 380-87. The advantage of this approach is that images are acquired as fast as possible (i.e., there is no delay between images), and as more periodic cycles are observed, the potential re-ordered frame rate becomes higher. However, a drawback of this approach is that there is no guarantee that the re-ordered images will adequately or evenly sample the periodic cycle of interest.

In accordance with the principles of the present invention, a diagnostic ultrasound imaging system is provided for acquiring images in relation to a periodic cycle so that a real time image sequence can be displayed of evenly temporally-spaced images. As the acquisition continues over more periodic cycles, a display sequence of evenly-spaced images can always be produced, with the temporal spacing of the evenly-spaced images becoming ever-finer as acquisition continues, enabling the replay of an image loop of ever-increasing frame rate of display. This is made possible by use of different acquisition triggers which are employed in the most efficient way to minimize delays between triggered acquisition sequences.

Figure 1:
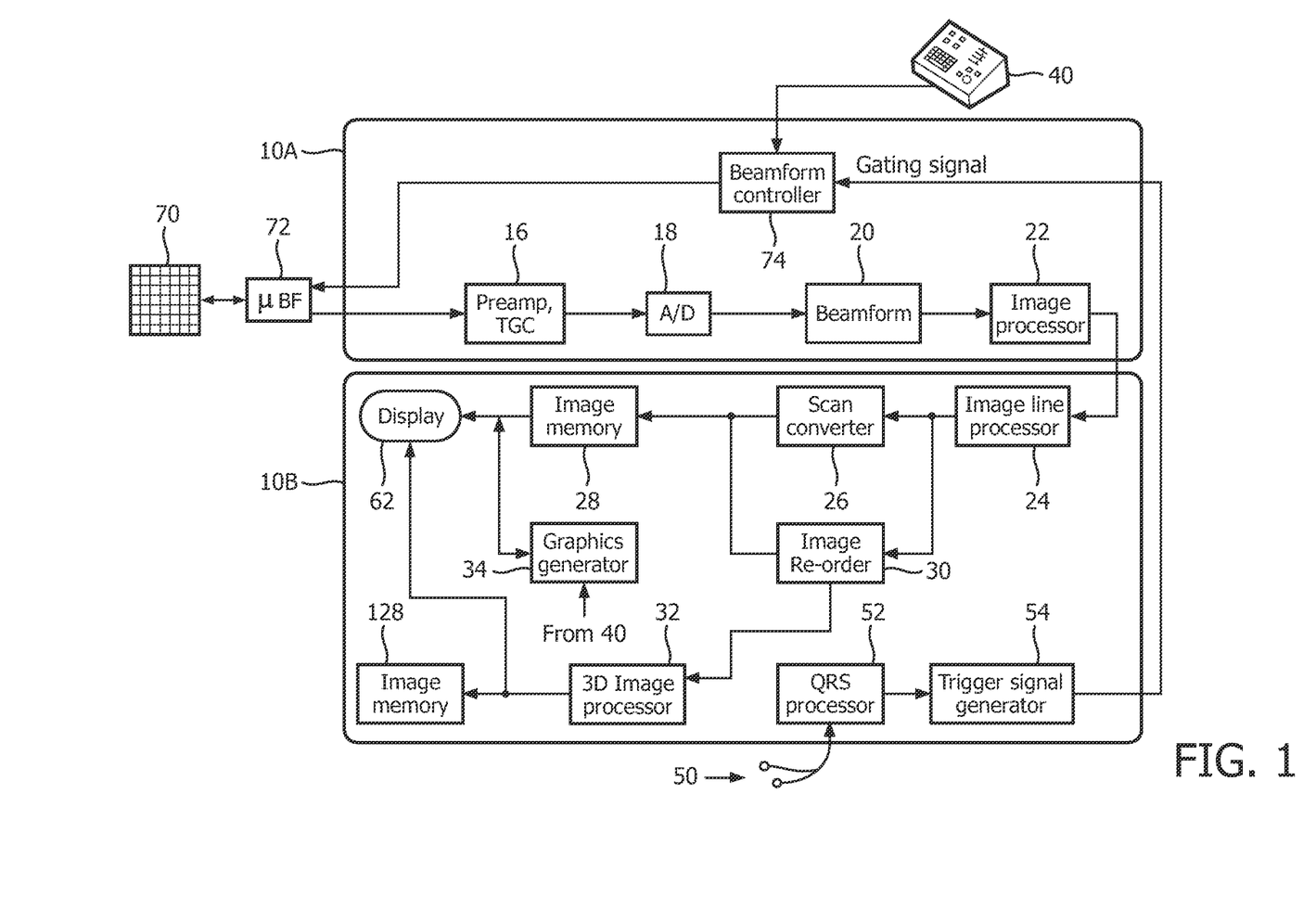
FIG. 1 illustrates in block diagram form an ultrasonic diagnostic imaging system constructed in accordance with the principles of the present invention.

Referring first to FIG. 1, an ultrasound system constructed in accordance with the principles of the present invention is shown in block diagram form. The illustrated ultrasound system operates through two major subsystems, a front end acquisition subsystem 10A and a display subsystem 10B. An ultrasound probe is coupled to the acquisition subsystem to transmit ultrasound waves and receive ultrasound echo signals. The probe may do this with a linear (one-dimensional) row of transducer elements, or may use a two-dimensional matrix array of transducer elements 70. The 2D matrix array and, if desired, the 1D array are operated by a micro-beamformer 72 located in the probe with the array transducer. The micro-beamformer contains circuitry which controls the signals applied to groups of elements of the array transducer 70 for acquisition and does some processing of the echo signals received by elements of each group. Micro-beamforming in the probe advantageously reduces the number of conductors in the cable between the probe and the ultrasound system and is described in U.S. Pat. No. 5,997,479 (Savord et al.) and in U.S. Pat. No. 6,436,048 (Pesque), and provides electronic steering and focusing of beams on transmit and during beam reception for high frame rate real-time (live) imaging.

The probe 70, 72 is coupled to the acquisition subsystem 10A of the ultrasound system. The acquisition subsystem includes a beamform controller 74 which is responsive to controls of the control panel 40 and provides control signals to the microbeamformer 72, instructing the probe as to the timing, frequency, direction and focusing of transmit and receive beams. In accordance with the principles of the present invention the control signals also comprise acquisition triggers to acquire images in specific time (phase) relation to a physiological gating signal. The beamform controller also controls the beamforming of echo signals received by the acquisition subsystem by its control of analog-to-digital (A/D) converters 18 and a beamformer 20. Partially beamformed echo signals received by the probe are amplified by preamplifier and TGC (time gain control) circuitry 16 in the acquisition subsystem, then digitized by the A/D converters 18. The digitized echo signals are formed into fully steered and focused beams by a main system beamformer 20. The echo signals are processed by an image processor 22 which performs digital filtering, B mode and M mode detection, and Doppler processing, and can also perform other signal processing such as harmonic separation, speckle reduction, and other desired image signal processing.

The echo signals produced by the acquisition subsystem 10A are coupled to the display subsystem 10B, which processes the echo signals for display in the desired image format on the display screen 62. The echo signals are processed by an image line processor 24, which is capable of sampling the echo signals, splicing segments of beams into complete line signals, and averaging line signals for signal-to-noise improvement or flow persistence. The image lines for a 2D (two dimensional) image are scan converted into the desired image format by a scan converter 26 which performs R-theta conversion as is known in the art. The scan converter can thus format rectilinear or sector image formats. The 2D image is then stored in an image memory 28 with other 2D images from which it can be displayed on the display 62. The images in memory are also overlaid with graphics to be displayed with the images, which are generated by a graphics generator 34 which is responsive to the user control 40 so that the graphics produced are associated with the images of the display. Individual images or image sequences can be stored in the image memory 28 for display of image loops or live sequences. Images for diagnosis can be stored on a networked image memory 128.

For real-time volumetric imaging the display subsystem 10B also includes a 3D (three dimensional) image rendering processor 32 which receives image lines from the image line processor 24 for the rendering of real-time three dimensional images. The 3D images can be displayed as live (real time) 3D images on the display 62 or coupled to the image memory 128 for storage of the 3D data sets for later review and diagnosis. In accordance with the principles of the present invention an image re-ordering processor 30 is provided which determines the order in which images acquired in accordance with the present invention will be displayed. The image re-ordering processor can do this by either storing acquired images in an image memory in the proper order from which they are displayed in the sequence in which they are stored, or by tagging each image with data that delineates the order in which it is to be displayed with other acquired images.

An ECG subsystem is provided for use when it is desirable to acquire images at particular phases of the heart cycle. ECG leads 50 can be adhesively attached to a patient and provide ECG signals for a QRS processor 52 which identifies the R-wave peak of each heartbeat. The timing of the R-wave is used to acquire images of a particular heart cycle. Images of the heart can be acquired at specific phases of the heart cycle by coupling the R-wave timing as a trigger signal from a trigger signal generator 54 to the beamform controller 74 and the controls of the control panel 40 used to select the desired heart phases at which heart phase-gated images are to be acquired by the selection of the appropriate acquisition triggers as described below.

The problems encountered in physiological gating, as previously described, are that when either of the conventional prospective or retrospective gating techniques are used, either the desired re-ordered frame rate needs to be pre-specified (prospective gating), large delays are included in the acquisition (prospective gating), or adequate (full) and even sampling of the periodic cycle is not assured (retrospective gating). It is undesirable to have the user pre-specify the re-ordered frame rate, as the user may decide during or after the acquisition that a higher frame rate than what was originally specified is needed. In this case, the user must perform another acquisition of images with a new pre-specified frame rate. Rather, it is desirable to have the imaging system automatically acquire images for progressively higher frame rates of evenly spaced images as acquisition progresses. Furthermore, large delays are undesirable during acquisition because longer acquisition times increase the possibility of patient or probe motion, which can render an acquisition sequence unuseable. Moreover, time is valuable in clinical settings and large delays translate into time that could otherwise be spent acquiring other image data. Also, it is unacceptable to acquire images with the intent of re-ordering them afterward, only to find out during or after the acquisition that adequate and even sampling of the periodic cycle of interest is not or was not obtained.

Figure 2:
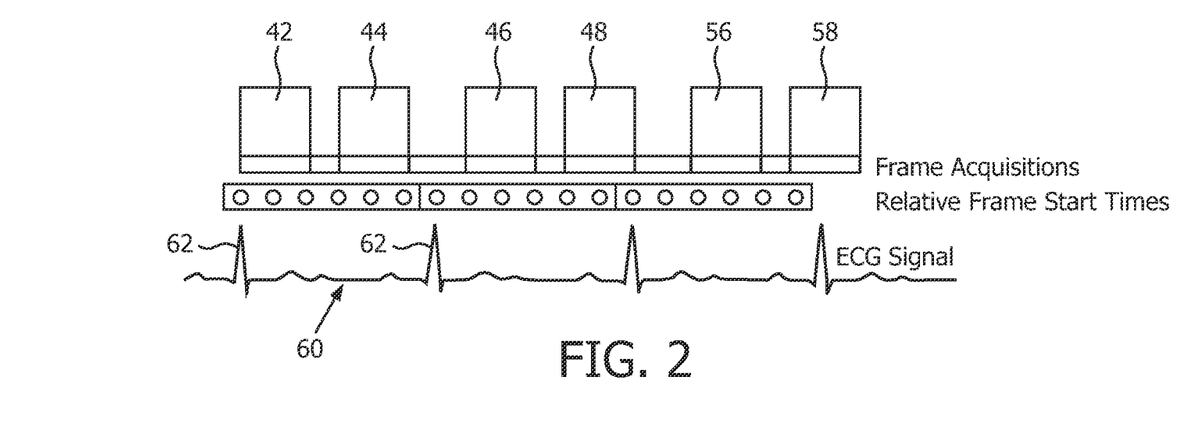
FIG. 2 illustrates an acquisition sequence using prospective gating in relation to an ECG signal.
Figure 3:
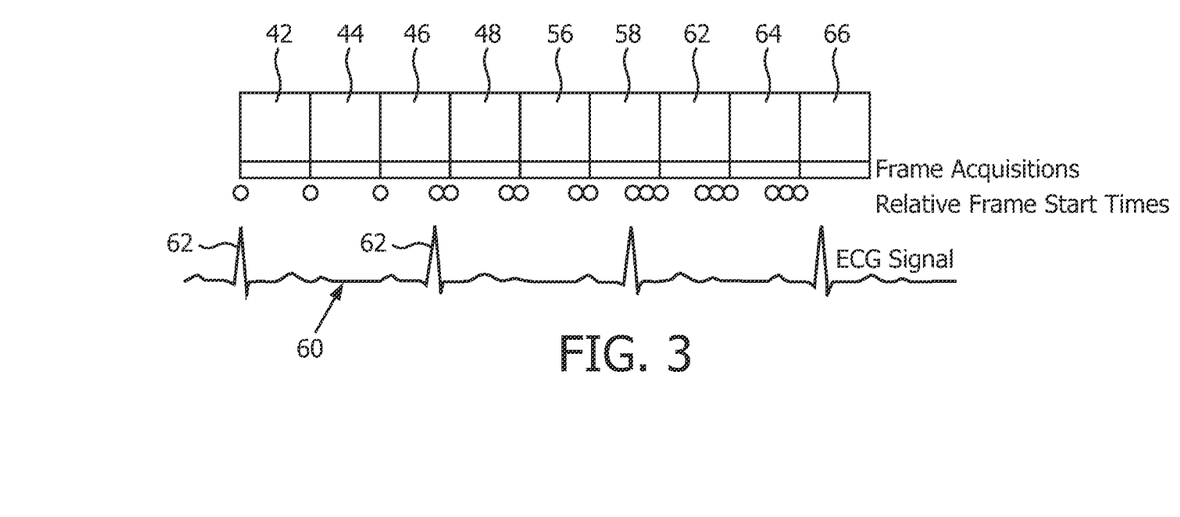
FIG. 3 illustrates an acquisition sequence using retrospective gating in relation to an ECG signal.

These problems may be understood more fully by referring the prospective and retrospective gating sequences of FIGS. 2 and 3, respectively. At the bottom of FIG. 2 is an ECG waveform 60 showing a periodically recurring QRS wave 62. The peak of the QRS wave is used as the timing reference for each new heart cycle. Above the ECG waveform is a row of dots marking six evenly spaced times during which it is desired to acquire an ultrasound image. Ultrasound images are acquired by transmitting a sequence of spatially adjacent scanlines to generate returning echo signals from along each scanline. The number of scanlines needed for a 2D image is typically 128 adjacent scanlines which are processed by the scan converter 26 to produce a 2D image. A 3D image is typically produced from many thousands of scanlines which scan a volumetric region of the body. Each rectangle 42 . . . 58 above the row of dots indicates the time during which the scanlines for one image are transmitted and echoes received. The time reference for each image in this example is taken as the start of the image acquisition. Dots which are darkened mark a phase of the six phases of the heartbeat for which an image has been acquired. It is seen that the first dot in the row is darkened to mark the acquisition of the first image 42. After this image has been acquired there is a period of deadtime during which no acquisition is done until the time of the fourth dot of the first heart cycle, at which time a second image 44 is acquired. There is then another period of deadtime until a third image is acquired at the second phase of the heart cycle during the second heart cycle. The darkened dot at the beginning of the second heart cycle shows that an image has already been acquired at this phase of the heartbeat, which was the first image 42. After the third image 46 is acquired there is another deadtime interval until the fourth image 48 is acquired at the fifth phase of the second heart cycle. This image acquisition interval extends to the start of the third heart cycle, after which there is another deadtime interval until the fifth image 56 is acquired at the third phase of the third heart cycle. Following the acquisition of this fifth image there is another deadtime interval until a sixth image 58 is acquired at the sixth phase of the third heart cycle. At the completion of acquisition of the sixth image 58 it is seen that six images have been acquired at six evenly spaced phases of the heartbeat, but it has taken three heart cycles to acquire all six images. These six images are re-ordered for display in a loop and are replayed in heart phase order, which is images 42, 46, 56, 44, 48, and 58. These six images are replayed in this order again and again, showing a beating heart moving in real time in heart phase order of the six temporally evenly spaced images. But it is seen that a substantial amount of deadtime was incurred during which no images were acquired, increasing the possibility that the acquisition will be interrupted by probe or patient motion which will require the acquisition to be performed again.

In FIG. 3 the image frames are acquired in rapid succession, one immediately following another. With the illustrated heart cycle duration and the time required to acquire each image it is seen that three images are acquired during the first heart cycle. But the timing is such that the image frames acquired during the second heart cycle fall immediately after the times of the first set of images, and in this example this second set of images 48, 56, and 58 fall one-eighteenth of a heart cycle after the first set. This phase-related acquisition continues with the third heart cycle as shown in the drawing. It is not until acquisition has been performed over six heart cycles that a full set of eighteen images are acquired at evenly spaced increments of a heart cycle. After the first heart cycle, one has to wait for another five heart cycles until a set of temporally evenly spaced images has been acquired.

The present invention improves upon these conditions through a combination of the concepts of both prospective and retrospective gating. The inventive acquisition mode is designed such that at any time during the acquisition, a set of frames are always present which are evenly spaced throughout the periodic heart cycle. As more periodic cycles are observed, the temporal offsets between re-ordered frames are made such that the offsets are nearly even between all re-ordered frames, and also made so that the offsets become smaller and smaller, resulting in higher and higher re-ordered frame rates for display. This allows the user to acquire during as few or as many cycles as desired, and the frames can always be re-ordered afterward such that the periodic cycle is adequately and evenly sampled. Because the inventive method requires only small delays, the acquisition mode operates in a near real-time or live mode, allowing the mode to be used for all real-time or live imaging, but having the advantage that any acquired sequence can be re-ordered into a higher frame rate sequence across a single periodic cycle.

The basic guidelines of an acquisition mode of the present invention are as follows:

a. Acquire images such that at all times during the acquisition the periodic signal is adequately (or fully) and evenly sampled.
b. Acquire images such that, as a larger number of periodic cycles are sampled, the temporal offset between re-ordered frames becomes smaller, resulting in a higher re-ordered frame rate.
c. Acquire images in as continuous a fashion as possible, with little or no delay between images in the acquisition.
d. Provide a display to the user during the acquisition indicating the potential re-ordered frame rate. Examples of the display would be one with a temporal unit number (Hz), and/or a plot (bar, line, pie chart, etc.), and/or a color (e.g., a color scale where blue is low frame rate and red is high frame rate) indicating the potential re-ordered frame rate. The display could also take the form, either separately or in addition to previously mentioned display methods, of showing the re-ordered frames in real-time by showing the previously acquired frame that is closest to the real-time temporal position relative to the periodic cycle. In this way, as more cycles are sampled and more frames acquired, this would have the effect of the image content appearing to become smoother and smoother during the real-time periodic cycle, providing a qualitative assessment of the re-ordered frame rate.

In a constructed implementation the acquisition mode is controlled by a set of triggers or interrupts. Triggers are characterized by a fixed temporal offset from the temporal landmark that occurs during each periodic cycle. In contrast to conventional gated acquisition, which use only a single trigger at a fixed temporal offset relative to the R-wave peak in the ECG signal, this implementation of the invention uses multiple triggers whose temporal offsets change throughout the acquisition. The triggers indicate when a free-running acquisition of a limited number of frames can begin within a given periodic cycle. These triggers are assigned as a group, where the size of the group is fixed for the length of an acquisition. The temporal offsets for the triggers are re-assigned only after every trigger from the group has been used. A trigger is considered to be "used" when, in any given periodic cycle, a free-running acquisition of frames begins at that particular trigger's relative temporal offset from the periodic temporal landmark. The temporal offsets of the triggers are re-assigned such that at any given time during the acquisition, the resulting temporal spacing of the acquired frames results in an adequate and even sampling of frames across the cardiac cycle. This can be done for instance in a simple example by assigning trigger temporal offsets as temporal midpoints of all previously used trigger offsets.

The following example illustrates this trigger assignment and re-assignment strategy in the context of gating of ultrasound frames using the R-peak in an ECG signal. This example is of the use of four triggers, but fewer triggers or more triggers can be used as desired. It should also be noted that while the ECG signal and R-wave peak are used in this example, any periodic signal and periodic temporal landmark could be used in their place.

Figure 4:
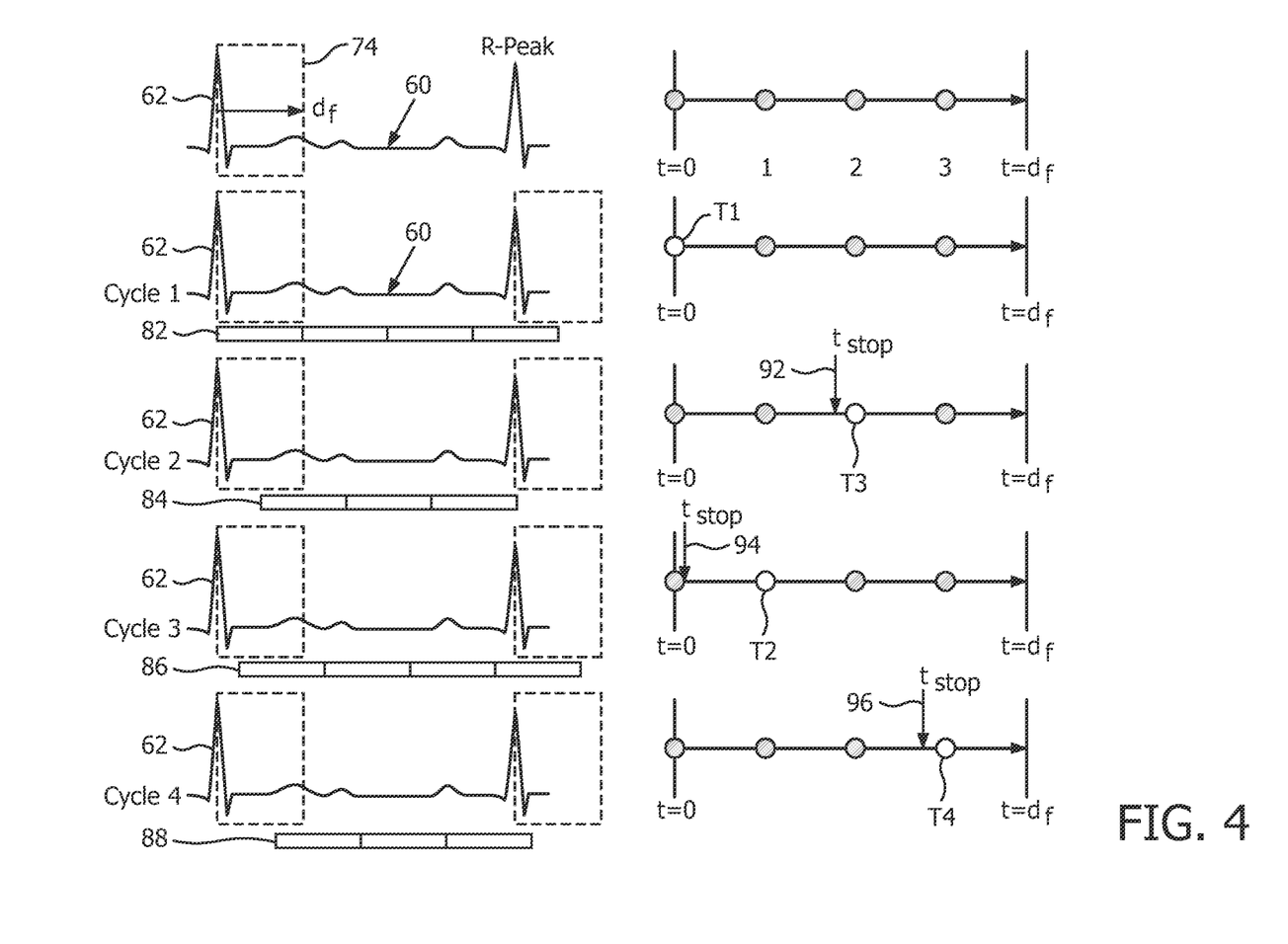
FIG. 4 illustrates an acquisition sequence in accordance with the present invention using four acquisition triggers.

In this example triggers are used to start a free-running acquisition during a single cardiac cycle. Frames are acquired continuously after the utilized trigger until another R-wave peak is observed. After the last image frame from the previous cycle has been acquired, the next available trigger is chosen. Accordingly, all triggers occur within one frame acquisition interval $d_f$ after the R-wave peak, where a frame acquisition interval is the length of time it takes to acquire a single frame. Triggers are also made to be equally spaced about the frame acquisition interval after the R-wave peak. In the example of FIG. 4 the four illustrated triggers start at times 0·$d_f/4$, $d_f/4$, $2d_f/4$, and $3d_f/4$ which are equally spaced over the $d_f$ acquisition interval. Equal spacing ensures that at any given time the set of frames acquired during the length of the acquisition can be re-ordered in a way that will result in adequate and even spacing across the cardiac cycle.

An illustration of this initial trigger assignment and subsequent frame acquisition over several cycles is shown in FIG. 4. In this example, four triggers are used, marked as T1, T2, T3 and T4. The four triggers start at different, evenly spaced phases of a frame acquisition interval $d_f$. In FIG. 4 the frame acquisition interval $d_f$ is indicated by a dashed box 74. The four evenly spaced phases at which these triggers start are marked by the circles on the right side of each ECG waveform 60 and occur at times t=0, 1, 2, and 3.

During the first heart cycle, Cycle 1, trigger T1 is used which acquires four images in immediate succession as indicated by the time bar 82 below the Cycle 1 ECG waveform. Acquisition of the first image frame begins at the time of the R-wave peak 62 of Cycle 1. The end of the time bar 82 shows that acquisition of the fourth frame by this trigger ends during the time interval at the start of Cycle 2. This ending time is shown as time $t_{stop}$ arrow 92 on the $d_f$ time line to the right of the Cycle 2 waveform. Since $t_{stop}$ occurs just before the start of trigger T3, T3 is used as the next trigger, providing virtually no delay between the end of trigger T1 and the start of trigger T3. Trigger T3 is then used during Cycle 2 to acquire three image frames as shown by time bar 84 below the Cycle 2 waveform. The completion of acquisition of the last image frame of trigger T3 is seen to occur just after the start of Cycle 3 as indicated by $t_{stop}$ marker 94. The next available unused trigger after $t_{stop}$ is T2, which is used for acquisition during Cycle 3. As time bar 86 illustrates, this trigger acquires four successive image frames, the last of which is complete during the latter portion of the df interval at the start of Cycle 4 as marked by $t_{stop}$ marker 96. Since this $t_{stop}$ time occurs just before the final unused trigger T4, this trigger is used to acquire the last four evenly spaced image frames of the acquisition sequence as indicated by time bar 88. This acquisition sequence thus acquires fifteen temporally evenly spaced image frames of a cardiac cycle with minimal deadtime between the end of each triggered continuous acquisition and the next unused trigger.

Figure 5:
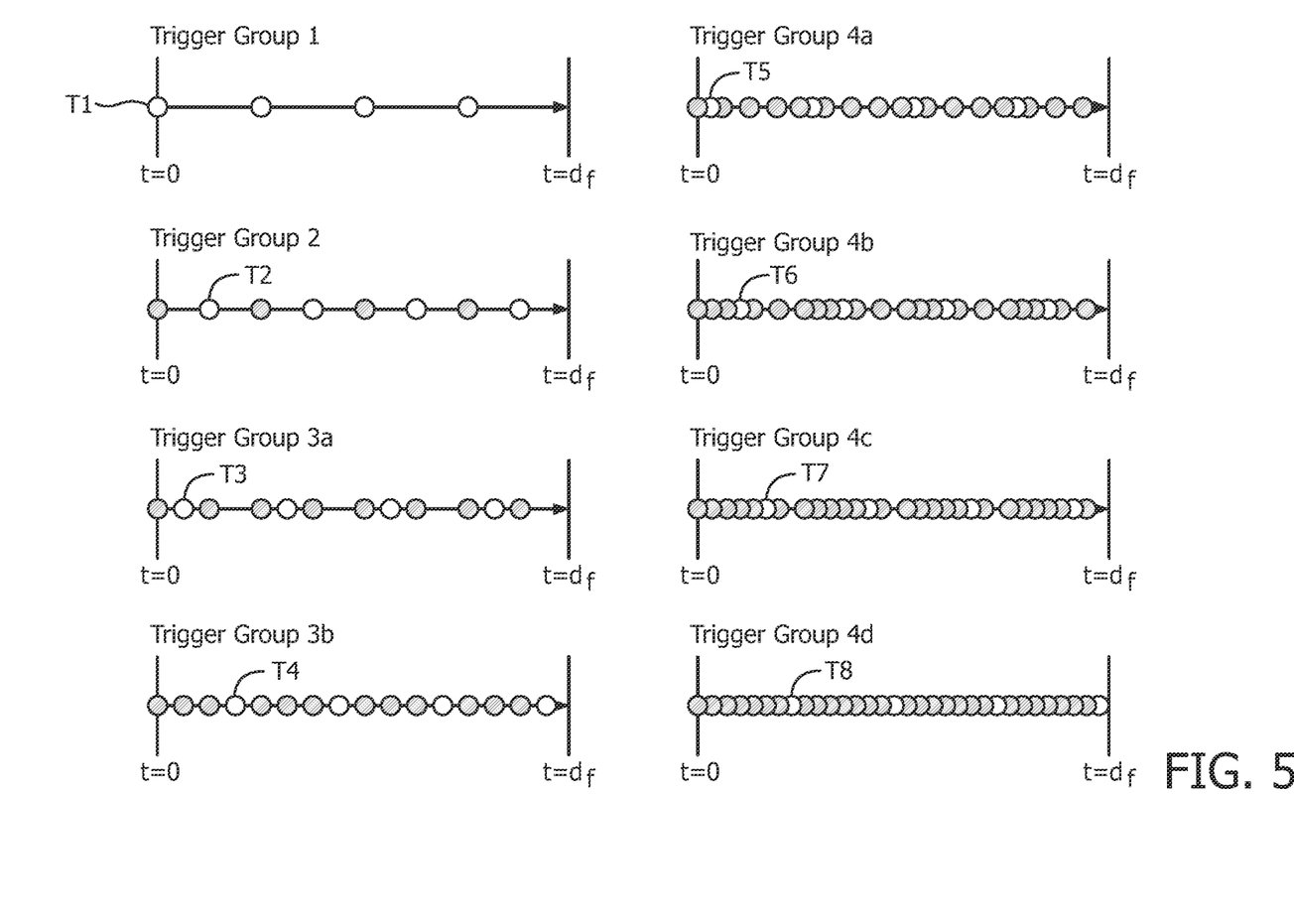
FIG. 5 illustrates an acquisition sequence of the present invention using four acquisition triggers and illustrating the availability of image loops for display of ever-increasing temporal frame rates of evenly-spaced images.

Triggers are re-assigned such that the number of triggers remains the same, the relative time between triggers remains constant, and the new trigger offset times temporally bisect the largest intervals as seen between any of the offsets previously used during the acquisition. An illustration of this is shown in FIG. 5 for the case where four triggers are used. As each trigger is the starting point of a free-running acquisition, it follows that the relative frame ordering for the frames across the cardiac cycle will be spaced similar to the depicted trigger start times, and so only the time frame between t=0 (R-wave peak), and t=$d_f$ (R-wave peak+$d_f$) is shown. Trigger T1, shown in the Trigger Group 1 line, is seen to sample the heart cycle at four evenly spaced times marked by the four circles on the time line. Trigger T2 samples the heart cycle with four more images at four points in time which are evenly spaced between the times of the T1 acquisitions as shown by the light circles of T2 sampling in Trigger Group 2. In Trigger Group 3a trigger T3 samples the heart cycle as indicated by the light circles. After these images have been acquired it can be seen that the heart cycle is not evenly temporally sampled as their are gaps between each group of three image frames. If acquisition were to be terminated at this point, either of the results of the T1 acquisition (Trigger Group 1) or the T1+T2 acquisition (Trigger Group 2) would be used for loop display, as both of those resulted in temporally even acquisition. In Trigger Group 3b the gaps of Trigger Group 3a are filled in by acquiring image frames with trigger T4. Once again, even sampling of the heart cycle is present, this time at a higher frame rate of display than previously. In Trigger Groups 4a, 4b, and 4c the heart cycle is sampled by triggers T5, T6, and T7. This increases the temporal density of the sampling of the heart cycle but it can be seen that sampling is not uniform over the heart cycle after any of these triggered acquisitions. If the acquisition were to be terminated during acquisition of any of these groups, the result of Trigger Group 3b would be used for a temporally even display. But when the heart cycle is sampled by acquisition with trigger T8 as shown in Trigger Group 4d, it is seen that temporally even sampling is restored this time at an even higher frame rate (32 image frames over a heart cycle) than before. It is seen that the acquisition process can be interrupted at anytime after the first trigger and still provide the user with an image sequence of temporally even sampling of the heart cycle.

It is thus seen that because a fixed number of triggers is used, there will be instances during the acquisition process where there is uneven sampling of the cardiac cycle even after all triggers from a group have been used. This is observed in Trigger Group 3a, 4a, 4b, and 4c. However, at any given time after the first trigger, there is an underlying subset of frames in which even sampling is observed. For instance, if acquisition is ended at Trigger Group 3a, the set of frames acquired in all trigger groups previous to this group are evenly sampled. Similarly, if acquisition is ended at Group 4a, 4b, or 4c, the set of all frames acquired in all trigger groups from Group 3b and prior are evenly sampled.

In an implementation of the present invention it is possible that during the acquisition, there are triggers that have not been used in a group but, due to the completion time of the frame acquired in the previous cycle, none of the triggers can be reached because $t_{stop} > t_{trigger,n}$ for all n, where $t_{trigger,n}$ is the relative offset of trigger n. These unused triggers are referred to as "unreachable." For instance, this would have occurred in the example shown in FIG. 4 if $t_{stop}$ in Cycle 4 would have occurred after the last trigger instead of just prior, making the last trigger T4 unreachable in Cycle 4. There are several ways to handle this scenario. A first option is to wait a complete cardiac cycle before acquiring any further frames. In doing so, when the next R-wave peak is observed, frame acquisition can begin at any trigger as no frames were previously being acquired during the current heart cycle. This option inserts a delay of one cardiac cycle into the acquisition, which may prove to be too great a delay. Another option is to dynamically change the triggers that still need to be used such that they occur at a time of $t_{trigger,n} + d_f$. This is the equivalent of adding one frame acquisition interval $d_f$ to the currently unused triggers. In doing so, any of the available triggers should be able to be used. For the triggers that do not end up being used after this change is made, their offset times are changed back to their previously assigned offset times. The drawback of this procedure is that it results in the "skipping" of the first frame that would have otherwise been acquired for the particular trigger that ends up being used, as compared to the original trigger offsets. Experiments using variable frame rates and numbers of triggers on real-patient ECG signals have shown this occurrence to be small. Still another option to handle this situation is to take measures to keep it from occurring. One way to do this would be to limit the number of frames acquired in the previous cardiac cycle using an estimate of the cardiac cycle time (made from previous cycles) and the acquisition frame rate. If it is estimated that the last frame will end at a time that will make all unused triggers unreachable in the next cycle, then the number of frames acquired in the previous cycle are controlled to stop acquiring frames at a time that will make the triggers reachable. Again, experiments have shown this occurrence to be small.

Those skilled in the art will recognize that the concepts of the present invention may be employed with different variables and modifications. For instance, one can allow triggers to reside at any time during the periodic cycle instead of a limited window, as described in the foregoing examples. Gating can be performed using multiple signals and/or multiple temporal landmarks. A variable number of triggers can be used throughout the acquisition, or variable trigger spacing can be employed throughout the acquisition. Frame acquisition can be stopped immediately after a temporal landmark is observed (e.g., an R-wave peak) which, while resulting in only a partial frame acquisition, will nonetheless prevent unused triggers from becoming unreachable. Triggers can also be assigned dynamically at any time during an acquisition and not just when the triggers in a group have all been used. Other variations will readily occur to those skilled in the art.

What is claimed is:

1. An ultrasonic diagnostic imaging system comprising:
   a source of gating signals for a physiological periodic cycle, the source of gating signals comprising a physiological sensor;
   an ultrasonic image acquisition subsystem configured to provide a plurality of triggers based on the gating signals to acquire ultrasound images at predetermined phases of the periodic cycle;
   an image processor configured to process acquired ultrasound images;
   an image sequencer configured to prepare a live sequence of images for display in relative phase sequence;
   a display, which is responsive to the image processor and image sequencer, configured to display the live sequence of images over the periodic cycle; and
   wherein the image acquisition subsystem is configured to acquire, in response to the plurality of triggers, a continuous sequence of images during the periodic cycle, wherein each trigger of the plurality starts at a different predetermined phase of the periodic cycle such that a temporal offset between the plurality of triggers progressively decreases as more periodic cycles are imaged by the ultrasonic image acquisition system, and wherein the image sequencer prepares the live sequence of images at a frame rate that progressively increases as more periodic cycles are imaged by the ultrasonic image acquisition subsystem.

2. The ultrasonic diagnostic imaging system of claim 1, wherein the plurality of triggers comprises a first image acquisition trigger configured to cause image acquisition at a first phase of the periodic cycle and a second image acquisition trigger configured to cause image acquisition at a second phase of a periodic cycle.

3. The ultrasonic diagnostic imaging system of claim 2, wherein the second phase is temporally halfway between the acquisition of first and second images by the first image acquisition trigger.

4. The ultrasonic diagnostic imaging system of claim 3, wherein the plurality of triggers comprises a third image acquisition trigger configured to cause image acquisition at a third phase of the periodic cycle, wherein the third phase is temporally halfway between the acquisition of an image by the first image acquisition trigger and the acquisition of an image by the second image acquisition trigger.

5. The ultrasonic diagnostic imaging system of claim 3, wherein after image acquisition by the first trigger at a phase of the periodic cycle, the image acquisition subsystem is configured to cause a next trigger which starts at a following starting phase of an unused trigger.

6. The ultrasonic diagnostic imaging system of claim 3, wherein the image acquisition subsystem is further configured to process the plurality of triggers in that, following use of the first trigger, the image acquisition subsystem acquires a sequence of acquired images which are temporally evenly spaced over a periodic cycle.

7. The ultrasonic diagnostic imaging system of claim 6, wherein image acquisition subsystem is further configured to process the plurality of triggers in that, following use of successive triggers after the first trigger, the image acquisition subsystem acquires a sequence of acquired images which are temporally evenly spaced and more closely temporally spaced than the sequence of images acquired by the first trigger.

8. The ultrasonic diagnostic imaging system of claim 1, wherein a trigger of the plurality is adapted to cause the image acquisition subsystem to stop acquiring images in the continuous sequence of images following a gating signal of a next successive periodic cycle.

9. The ultrasonic diagnostic imaging system of claim 1, wherein the periodic cycle comprises a heart cycle and wherein the plurality of gating signals are received from an ECG electrode.

10. The ultrasonic diagnostic imaging system of claim 1, wherein the periodic cycle comprises a respiratory cycle.

11. The ultrasonic diagnostic imaging system of claim 1, wherein the display is further adapted to display a live sequence of images over a periodic cycle and to continuously replay the live sequence of images from beginning to end until stopped.

12. The ultrasonic diagnostic imaging system of claim 1, wherein the live sequence displayed by the display further comprises a sequence of acquired images which has been ordered by the image sequencer, wherein the display further displays a frame rate of the live sequence ordered by the image sequencer.

13. The ultrasonic diagnostic imaging system of claim 12, wherein the frame rate is displayed numerically, graphically, or by a color.

14. The ultrasonic diagnostic imaging system of claim 1, wherein all of the triggers start an acquisition sequence within one frame acquisition interval after a physiological gating signal.

15. The ultrasonic diagnostic imaging system of claim 14 wherein all of the triggers start an acquisition sequence at evenly spaced intervals of a frame acquisition interval.

16. The ultrasonic diagnostic imaging system of claim 1, wherein the plurality of triggers comprises at least three triggers.

* * * * *